(12) United States Patent
Tsubouchi et al.

(10) Patent No.: US 7,128,538 B2
(45) Date of Patent: Oct. 31, 2006

(54) CENTRIFUGAL FLUID PUMP APPARATUS

(75) Inventors: Takeshi Tsubouchi, Ann Arbor, MI (US); Takehisa Mori, Kanagawa (JP)

(73) Assignee: Terumo Corporation, Tokyo (JP)

( * ) Notice: Subject to any disclaimer, the term of this patent is extended or adjusted under 35 U.S.C. 154(b) by 552 days.

(21) Appl. No.: 10/613,068

(22) Filed: Jul. 7, 2003

(65) Prior Publication Data
US 2005/0008496 A1     Jan. 13, 2005

(51) Int. Cl.
F04B 49/00         (2006.01)
(52) U.S. Cl. .................. 417/12; 417/44.1; 604/151
(58) Field of Classification Search ............. 417/420, 417/423.7, 427.12, 42, 44.1, 44.11, 37; 604/6.11, 604/131, 151, 65, 67; 600/16, 17
See application file for complete search history.

(56) References Cited

U.S. PATENT DOCUMENTS

| | | | |
|---|---|---|---|
| 5,683,231 A * | 11/1997 | Nakazawa et al. .......... | 417/420 |
| 5,947,703 A | 9/1999 | Nojiri et al. | |
| 6,030,188 A * | 2/2000 | Nojiri et al. ................ | 417/420 |
| 6,071,093 A | 6/2000 | Hart | |
| 6,227,817 B1 * | 5/2001 | Paden ......................... | 417/356 |
| 6,280,156 B1 * | 8/2001 | Wirz et al. .................. | 417/420 |
| 6,547,530 B1 * | 4/2003 | Ozaki et al. ............... | 417/44.1 |
| 2001/0016170 A1 * | 8/2001 | Ozaki et al. ................ | 417/420 |
| 2001/0053330 A1 * | 12/2001 | Ozaki ......................... | 417/420 |

FOREIGN PATENT DOCUMENTS

| | | |
|---|---|---|
| EP | 1 027 898 A1 | 8/2000 |
| EP | 1 070 510 A2 | 1/2001 |

* cited by examiner

*Primary Examiner*—Tae Jun Kim
*Assistant Examiner*—Vikansha Dwivedi
(74) *Attorney, Agent, or Firm*—Buchanan Ingersoll & Rooney PC

(57) ABSTRACT

A centrifugal fluid pump apparatus includes a control mechanism including an emergency impeller rotation function. The emergency impeller rotation function includes a rotation termination function when the failure detection function detects a failure; impeller magnetic counterforce application function to apply a current to the electromagnet sufficient to overcome the magnetic attraction force of the rotor to the impeller caused by the magnet; hydrodynamic levitation control detection function to detect rotation of the impeller and the rotor by using a motor current monitored by the motor current monitoring function; motor speed control function for increasing the motor speed up to a predetermined value after the hydrodynamic levitation control detection function detects that the hydraulic bearing coupling between the impeller and the rotor has been made; and impeller magnetic counterforce termination function to terminate current to the electromagnet once the predetermined impeller rotation speed is reached.

15 Claims, 9 Drawing Sheets

CENTRIFUGAL FLUID PUMP APPARATUS

BACKGROUND OF THE PRESENT INVENTION

The present invention relates to a centrifugal fluid pump apparatus, and in particular to a centrifugal fluid pump for pumping a medical fluid, such as blood.

In recent medical treatment, centrifugal blood pumps are increasingly used in artificial heart/lung units for extracorporeal blood circulation. Centrifugal pumps of the magnetic coupling type wherein a driving torque from an external motor is transmitted to an impeller through magnetic coupling are commonly used because the physical communication between the blood chamber of the pump and the exterior can be completely excluded and invasion of bacteria is prevented. The centrifugal blood pump includes a housing having a blood inlet port and a blood outlet port and an impeller rotatably accommodated in the housing to feed blood by a centrifugal force generated during its rotation. The impeller, having a permanent magnet disposed therein, is rotated by a rotor having magnets for attracting the magnet of the impeller thereto and by a rotational torque generation mechanism having a motor for rotating the rotor. The impeller rotates without contacting the housing, with the impeller being attracted to the side opposite to the rotor-disposed side by a magnetic force. This state is termed a magnetic levitation state.

When a failure or malfunction occurs in the control system of the magnetic bearing of the conventional centrifugal pump, however, it is impossible to maintain the function of the centrifugal pump by rotating the impeller.

The centrifugal pump of a magnetic levitation type has three sensors for detecting the position of the impeller and three impeller attraction electromagnets. In the control of the magnetic bearing to be executed in the centrifugal pump, the position of the impeller is controlled by controlling electric current to be applied to the electromagnets, based on information of the impeller provided by the sensors for detecting the position of the impeller. Thus, if devices forming a portion of the control system should fail, for example, if cables for the position sensors and for the electromagnets break, the control system will encounter a failure and proper control cannot be accomplished. Thus, it is difficult to rotate the impeller by means of the magnetic bearing in a magnetic levitation state under these circumstances.

It is an object of the present invention to provide a centrifugal fluid pump apparatus allowing rotation of an impeller without substantial contact between the impeller and an inner surface of a housing by utilizing pressure generated by a hydrodynamic bearing when the control system of the magnetic bearing encounters a failure or malfunction, to thereby maintain feeding of a liquid.

SUMMARY OF THE PRESENT INVENTION

The object described above is attained by the following centrifugal fluid pump apparatus.

The centrifugal fluid pump apparatus comprises a pump body in which an impeller rotates without contacting a housing; and a control mechanism for said pump body, said pump body including: said housing having a blood inlet port and a blood outlet port; a centrifugal pump section including an impeller having a first magnetic material and a second magnetic material and rotating in said housing to feed a fluid by a centrifugal force generated during its rotation; an impeller rotational torque generation section including a rotor having a magnet for attracting said first magnetic material of said impeller and a motor for rotating said rotor; an impeller position control section having an electromagnet for attracting said second magnetic material of said impeller; a position sensor for detecting a position of said impeller; and hydrodynamic bearing means provided on an inner surface of said housing at a side of said rotor or on a surface of said impeller at a side of said rotor, said control mechanism comprising: a position sensor output monitoring function or an electromagnet current monitoring function; a motor current monitoring function; a failure detection function for determining a failure of the sensor by using said position sensor output monitoring function or a failure of the electromagnet by using said electromagnet current monitoring function; and an emergency impeller rotation function operating when said failure detection function detects the failure of the sensor or the failure of the electromagnet to rotate said impeller by utilizing said hydrodynamic bearing means without substantial contact between said impeller and said housing, wherein said emergency impeller rotation function has: rotation termination function of terminating current to the motor and the electromagnet when the failure detection function detects a failure to thereby terminate rotation of the rotor and the impeller; impeller magnetic counterforce application function to apply a current to the electromagnet sufficient to overcome the magnetic attraction force of the rotor to the impeller caused by the magnet; hydrodynamic levitation control detection function of detecting rotation of the impeller and the rotor by using a motor current monitored by the motor current monitoring function; motor speed control function for increasing the motor speed and hence the impeller rotation speed up to a predetermined value after the hydrodynamic levitation control detection function detects that the hydraulic bearing coupling between the impeller and the rotor has been made; and impeller magnetic counterforce termination function to terminate current to the electromagnet once the predetermined impeller rotation speed is reached.

BRIEF DESCRIPTION OF THE DRAWINGS

The above and other objects, features and advantages of the present invention will be better understood by reading the following description, taken in conjunction with the accompanying drawings.

DETAILED DESCRIPTION OF THE PREFERRED EMBODIMENTS

Figure 1:
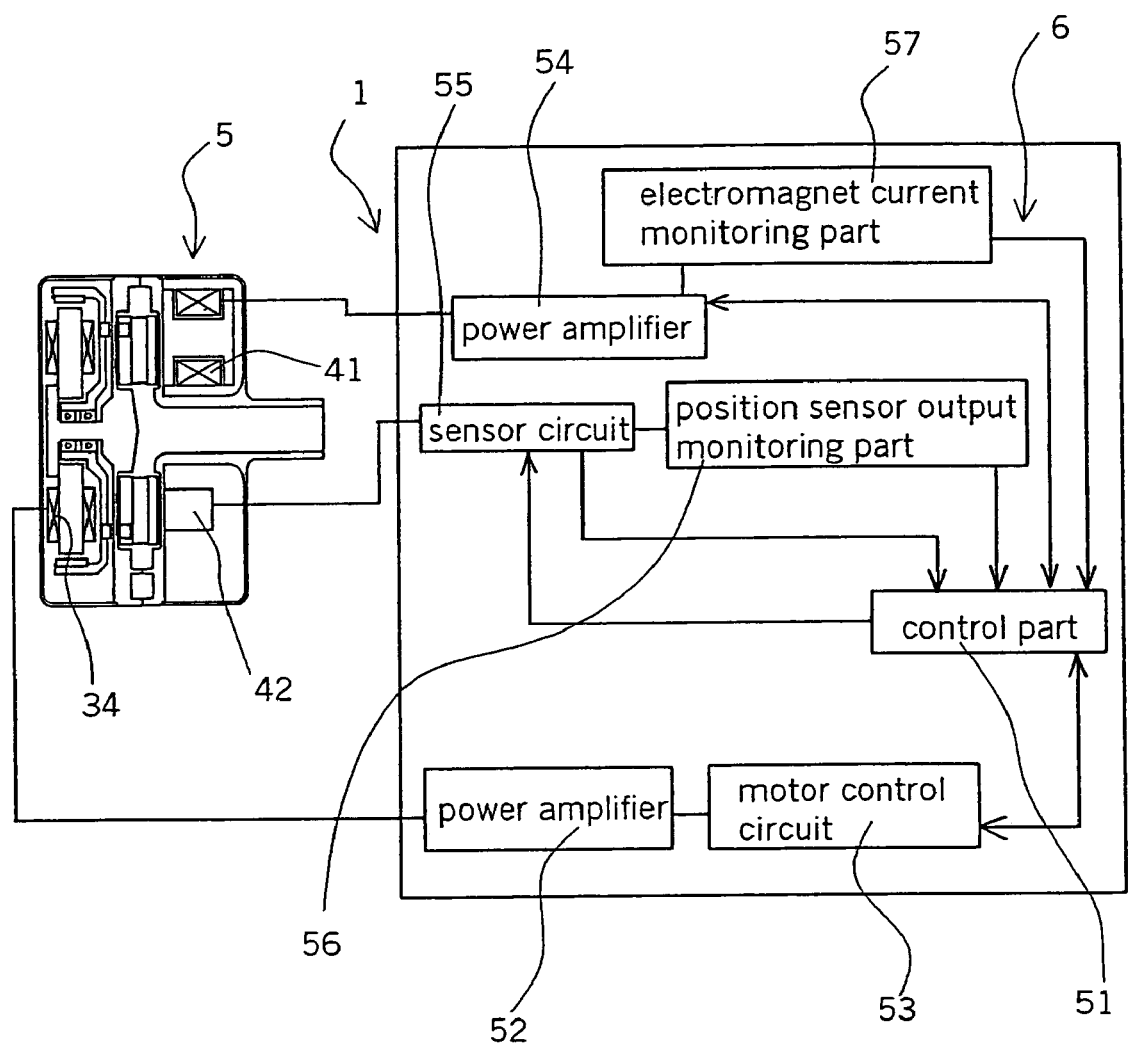
FIG. 1 is a block diagram showing a centrifugal fluid pump apparatus according to an embodiment of the present invention.
Figure 2:
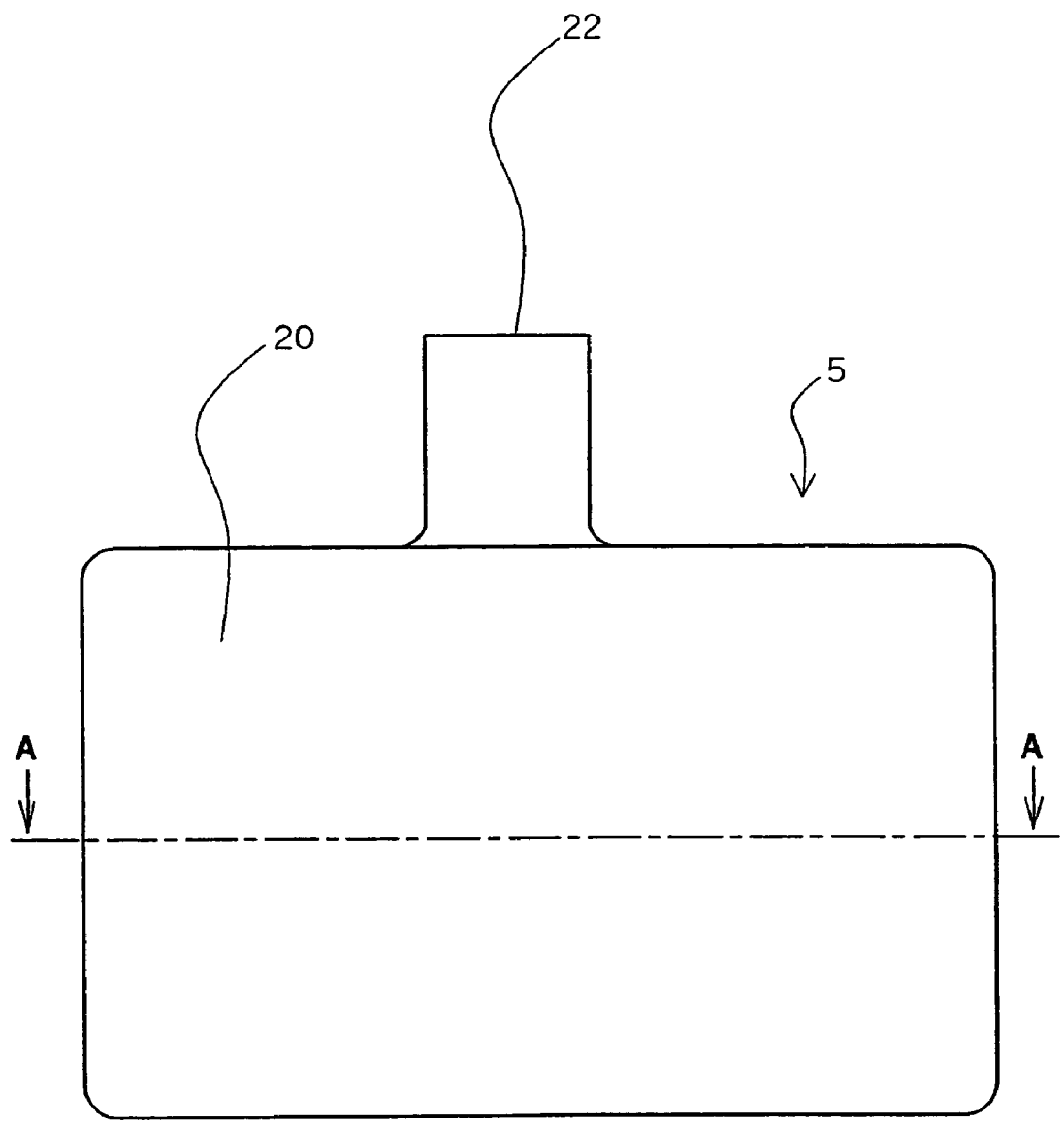
FIG. 2 is a front view showing an example of the body of the centrifugal fluid pump apparatus of the present invention.

An embodiment of the centrifugal fluid pump apparatus according to the present invention is described below with reference to the drawings. A centrifugal fluid pump apparatus of the present invention is generally indicated by reference numeral 1. Centrifugal fluid pump apparatus 1 includes a pump body 5 in which an impeller 21 rotates without contacting a housing 20; and a control mechanism 6 for the body 5.

Referring to FIGS. 2–6, the pump body 5 includes the housing 20 having a blood inlet port 22 and a blood outlet port 23; a centrifugal fluid pump section 2 including an impeller 21 having a first magnetic material 25 and a second magnetic material 28 disposed therein and rotating in the housing 20 to feed a fluid by a centrifugal force generated during its rotation; an impeller rotational torque generation section 3 including a rotor 31 having a magnet 33 for attracting thereto the first magnetic material 25 of the impeller 21 and a motor 34 for rotating the rotor 31; an impeller position control section 4 having an electromagnet 41 (electromagnet for attracting the second magnetic material 28 of the impeller 21 thereto) for attracting the impeller 21 thereto, a position sensor 42 (position sensor for detecting the position of the second magnetic material 28 of the impeller 21) for detecting the position of the impeller 21, and a groove 38 for hydrodynamic bearing provided on an inner surface of the housing 20 at the side of the rotor 31 or a surface of the impeller 21 at the side of the rotor 31.

The control mechanism 6 has a position sensor output monitoring part (position sensor output monitoring function) 56, a motor current monitoring function or an electromagnet current monitoring function 57, and a failure detection function. The failure detection function for determining a failure of the sensor 42 by using said position sensor output monitoring function or a failure of the electromagnet 41 by using said electromagnet current monitoring function.

As shown in FIG. 1, it is preferable that the control mechanism 6 has the position sensor output monitoring function 56, the electromagnet current monitoring function 57, the motor current monitoring function, and the failure detection function of determining whether the sensor has a failure by using the position sensor output monitoring function 56 and whether the electromagnet has a failure by using the electromagnet current monitoring function 57.

The centrifugal fluid pump apparatus 1 has an emergency impeller rotation function that operates when the failure detection function has detected that the sensor or the electromagnet has a failure to rotate the impeller 21 by utilizing the groove 38 for hydrodynamic bearing without substantial contact between the impeller 21 and the housing 20.

The emergency impeller rotation function includes a rotation termination function of terminating current to the motor and the electromagnet 41 when the failure detection function detects a failure to thereby terminate rotation of the rotor 31 and the impeller 21; impeller magnetic counterforce application function to apply a current to the electromagnet 41 sufficient to overcome the magnetic attraction force of the rotor 31 to the impeller 21 caused by the permanent magnet 33; a hydrodynamic levitation control detection function detecting that a hydraulic bearing coupling between the impeller and the rotor has been made and that there is rotation of the impeller, i.e., there is a magnetic rotational coupling achieved under hydraulic bearing conditions, by using a motor current monitored by the motor current monitoring function; a motor speed control function for increasing the motor speed and hence the impeller rotation speed up to a predetermined value (for example, gradually, namely, successively or stepwise) after the hydrodynamic levitation control detection function detects that the hydraulic bearing coupling between the impeller and the rotor has been made; and impeller magnetic counterforce termination function to terminate current to the electromagnet 41 once the predetermined impeller rotation speed is reached.

That is, when the sensor or the electromagnet has a failure, the centrifugal fluid pump apparatus 1 of the present invention has the function of shifting from the non-contact (magnetic) rotational coupling of the impeller by means of the magnetic bearing to the non-contact (magnetic) rotational coupling of the impeller by means of the hydrodynamic bearing, i.e., the groove, that generates a pressure.

In the rotation of the impeller 21 made by means of the groove for hydrodynamic bearing, it is necessary to balance the magnetic attraction force acting between the impeller and the rotor, due to the presence of the permanent magnet 33, with the pressure generated by the groove for hydrodynamic bearing in a direction opposite to the direction of the magnetic attraction force. To do so, rotation of the impeller and the rotor is essential. Therefore, in the case where the control system of the magnetic bearing has encountered a failure, and thus the magnetic levitation state of the impeller and the rotor are uncoupled from each other, even machining of the groove for hydrodynamic levitation control does not allow the shift from the rotation of the impeller by means of the magnetic bearing to the rotation thereof by means of the groove for hydrodynamic bearing because of the large attraction forces and resulting frictional forces caused by the unbalanced attraction of the permanent magnet 33 to the impeller.

Description will be made of an embodiment of the centrifugal fluid pump apparatus of a type having the position sensor output monitoring function 56 and the electromagnet current monitoring function 57 shown in FIG. 1 and capable of making determination as to whether the sensor and the electromagnet have a failure.

As shown in FIGS. 2–6, the body 5 has the housing 20 having the blood inlet port 22 and the blood outlet port 23, the centrifugal fluid pump section 2 having the impeller 21 rotating inside the housing 20 to feed blood by a centrifugal force generated during its rotation, the impeller rotational torque generation section (non-contact type magnetic bearing constructing section) 3 for the impeller 21, and the impeller position control section (contact type magnetic bearing constructing section) 4 for the impeller 21.

Figure 4:
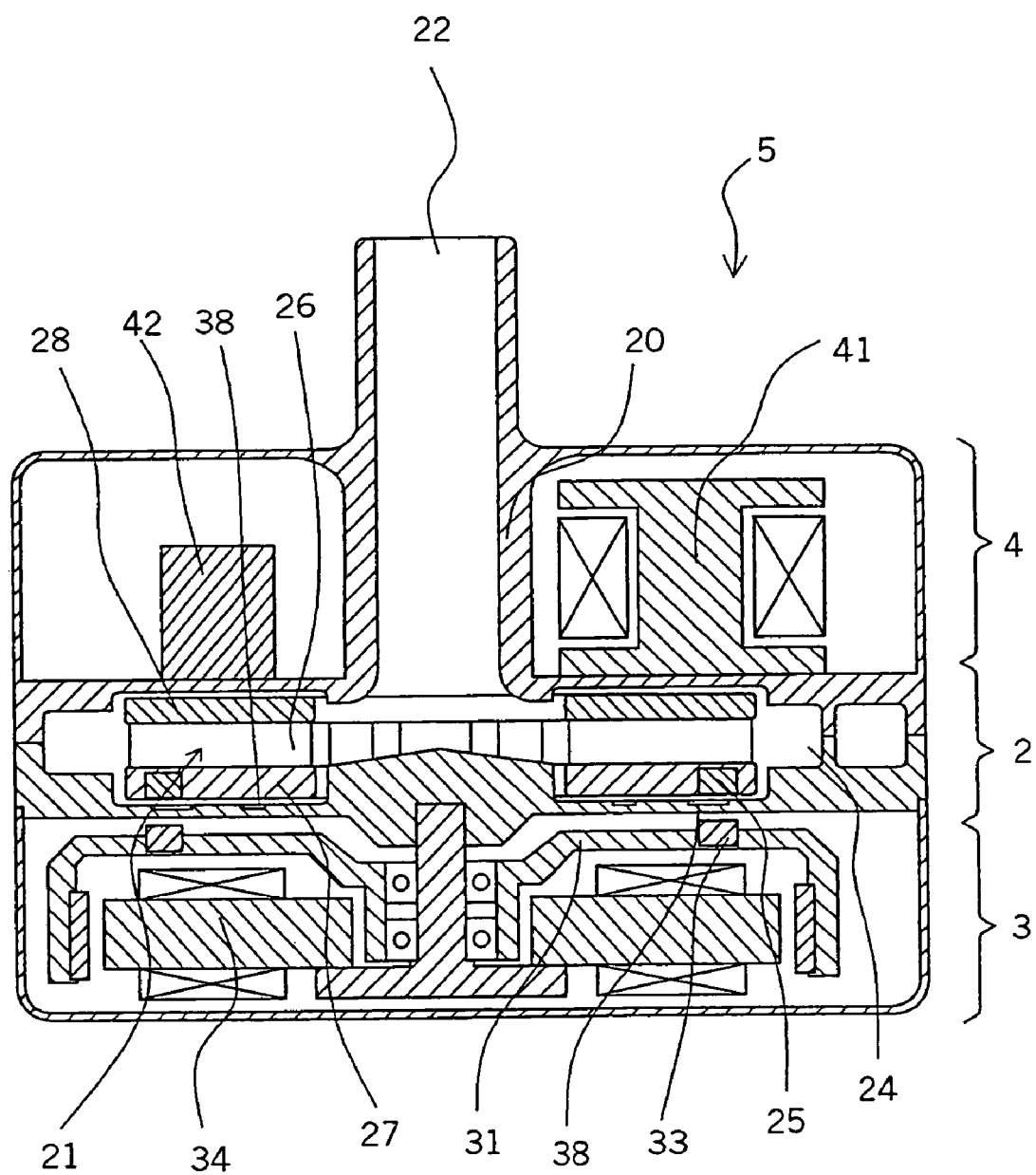
FIG. 4 is a vertical sectional view showing the body of the centrifugal fluid pump apparatus of the embodiment shown in FIG. 2.

As shown in FIG. 4, at a normal time, the impeller 21 rotates without contacting the inner surface of the housing 20, with the impeller 21 held at a predetermined position inside the housing 20 by the operation of the non-contact type magnetic bearing constructing section 3 and that of the contact type magnetic bearing constructing section 4.

The housing 20 has the blood inlet port 22 and the blood outlet port 23 and is formed of a non-magnetic material. The housing 20 accommodates a blood chamber 24 communicating with the blood inlet and outlet ports 22 and 23. The housing 20 also accommodates the impeller 21 therein. The blood inlet port 22 projects substantially vertically from the vicinity of the center of the upper surface of the housing 20.

Figure 3:
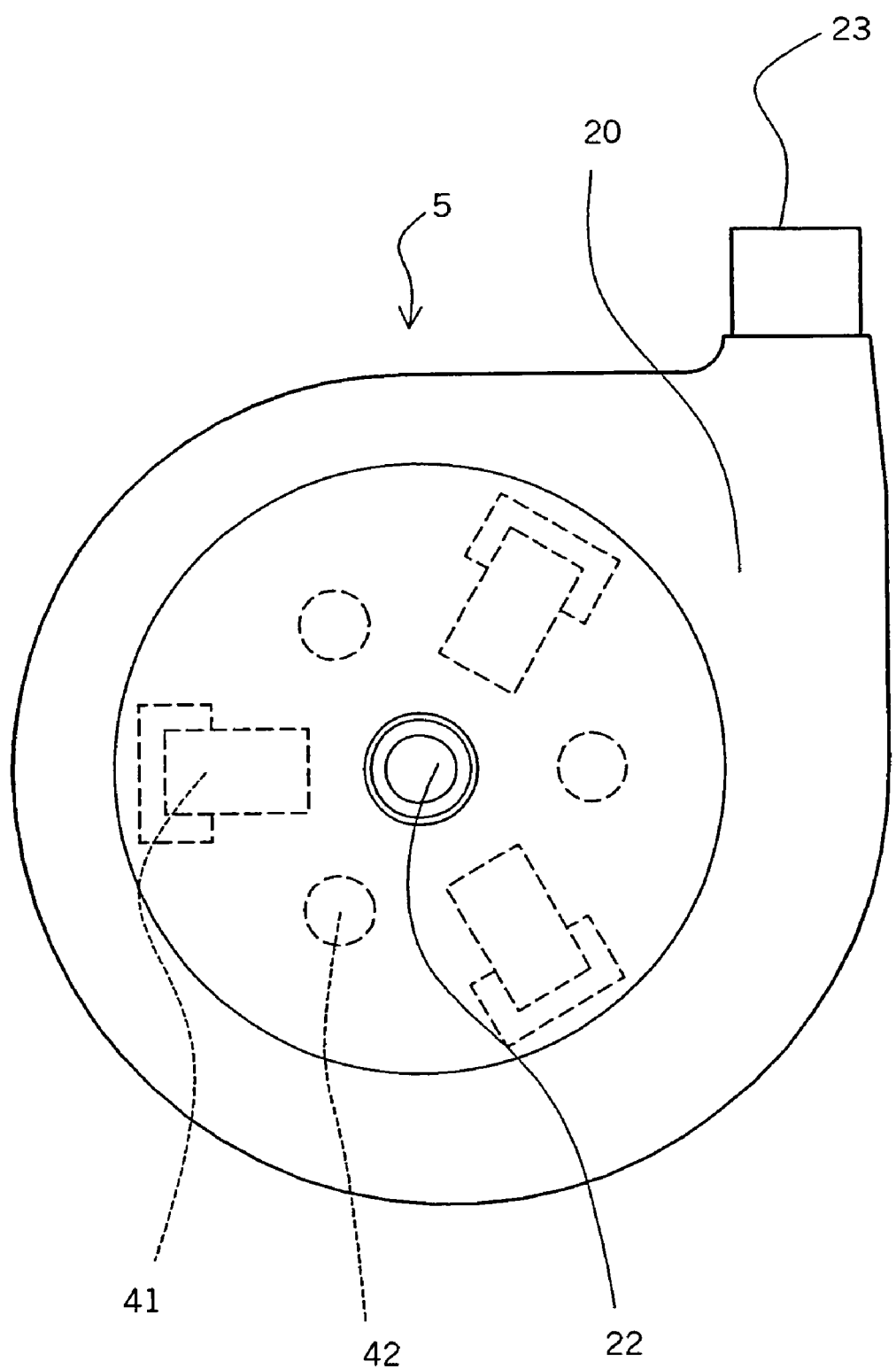
FIG. 3 is a plan view showing the body of the centrifugal fluid pump apparatus of the present invention shown in FIG. 2.
Figure 5:
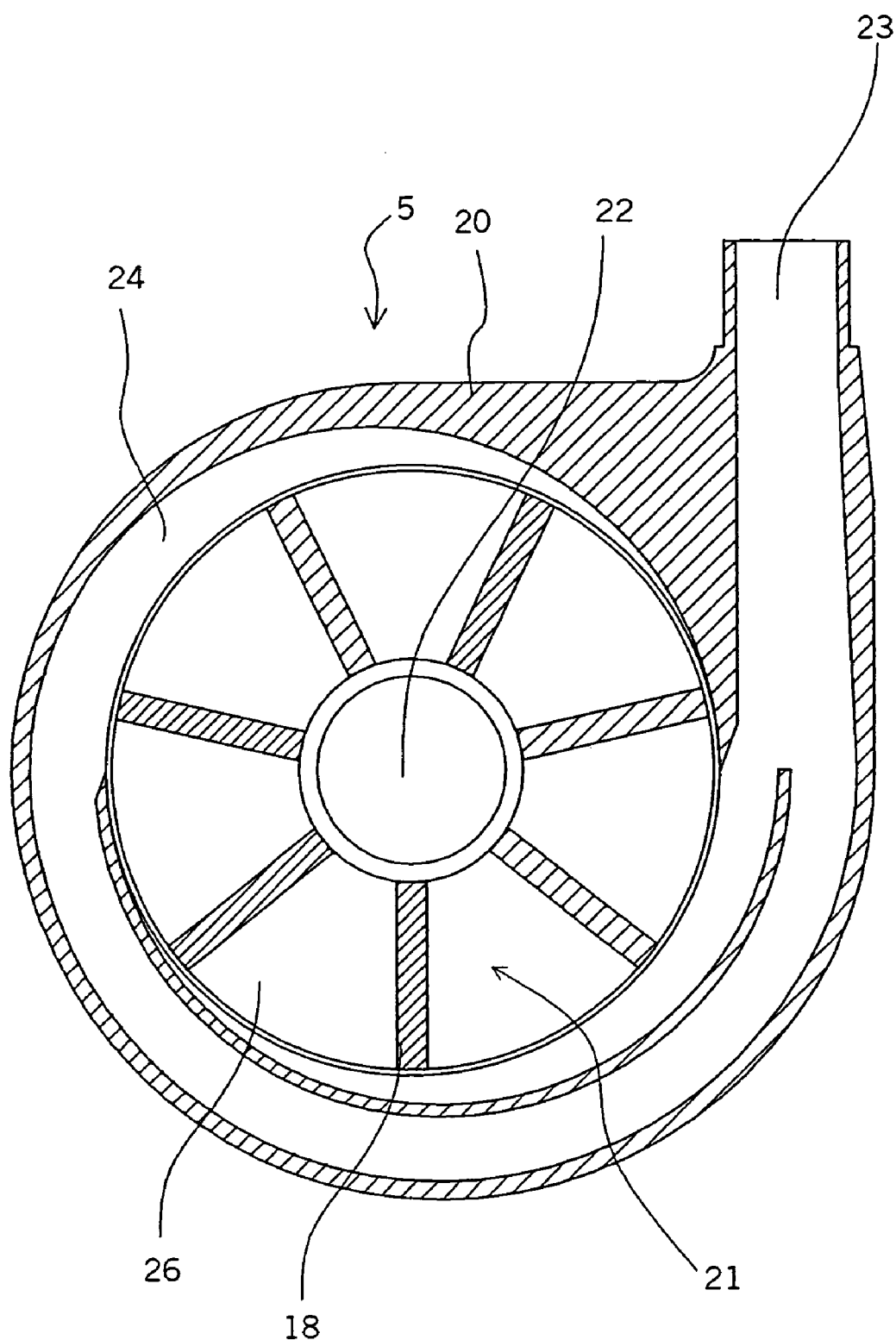
FIG. 5 is a sectional view taken along a line A—A in FIG. 2 showing the body of the centrifugal fluid pump apparatus.

As shown in FIGS. 3 and 5, the blood outlet port 23 projects tangentially from a side surface of the approximately cylindrical housing 20.

As shown in FIG. 5, the disc-shaped impeller 21 having a through-hole in the center thereof is accommodated inside the blood chamber 24 formed inside the housing 20. As shown in FIG. 4, a preferred embodiment of the impeller 21 includes an annular plate-shaped member (lower shroud) 27 forming the lower surface thereof, an annular plate-shaped member (upper shroud) 28 forming the upper surface thereof and opening at the center thereof, and a plurality of (for example, seven) vanes 18 formed between the lower shroud 27 and the upper shroud 28. A plurality of (for example, seven) blood passages 26 partitioned from one another by the adjacent vanes 18 is formed between the lower shroud 27 and the upper shroud 28. As shown in FIG. 5, each of the blood passages 26 communicates with the center opening of the impeller 21 and extends from the center opening of the impeller 21 to its periphery, with each of the blood passages 26 becoming gradually larger in the width thereof. In other words, the vanes 18 are formed between the adjacent blood passages 26. In the illustrated embodiment, the vanes 18 and blood passages 26 are spaced at equiangular intervals and in substantially the same shape.

As shown in FIG. 4, a plurality (for example, 24) of the first magnetic materials 25 (for example permanent magnet, follower magnet) are embedded in the impeller 21. In this embodiment, the first magnetic materials 25 are embedded in the lower shroud 27. The embedded first magnetic materials 25 are provided so that the impeller 21 is attracted toward the side opposite to the side where the blood inlet port 22 (in other words, a side of the rotor 31) is disposed by a permanent magnet 33 provided in the rotor 31 of the rotational torque generation section 3 to be described later and that the rotational torque is transmitted from the rotational torque generation section 3 to the impeller 21.

The magnetic levitation coupling, to be described later, between the impeller 21 and the rotor 31 is ensured by embedding a plurality of the first magnetic materials 25 in the impeller 21. It is preferable that each of the first magnetic materials 25 (permanent magnet) is circular in a horizontal cross section. Although, it is also possible to use a ring-shaped magnet having multi-poles (for example, 24 poles). In other words, a plurality of small magnets may be arranged in the shape of a ring in such a way that positive and negative poles alternate with each other.

The impeller 21 further includes the second magnetic member 28 which itself constitutes the upper shroud or which is provided inside the upper shroud. In this embodiment, the entire upper shroud is constructed of the second magnetic member 28. The second magnetic member 28 is provided so that the electromagnet 41 of the impeller position control section 4, to be described later, attracts the impeller 21 magnetically toward the blood inlet port 22. The second magnetic member 28 is made of magnetic stainless steel.

The impeller position control section 4 and the rotational torque generation section 3 constitute a non-contact type magnetic bearing, which magnetically attracts the impeller 21 from opposite directions. Thereby the impeller 21 is held steadily at a proper position not in contact with the inner surface of the housing 20 and rotates inside the housing 20 without contacting its inner surface.

As shown in FIG. 4, included in the rotational torque generation section 3 are the rotor 31 accommodated in the housing 20 and a motor 34 for rotating the rotor 31. The rotor 31 has a plurality of permanent magnets 33 disposed on a surface thereof at the side of the centrifugal fluid pump section 2. The center of the rotor 31 is fixedly secured to the rotational shaft of the motor 34. A plurality of the permanent magnets 33 are equiangularly distributed in accordance with the arrangement mode (number and position) of the permanent magnets 25 of the impeller 21.

The impeller rotation torque generation section 3 is not limited to the illustrated one having the rotor and motor. For example, a plurality of stator coils may be used as the impeller rotation torque generation section 3 as long as they can attract the permanent magnets 25 of the impeller 21 thereto and drive the impeller 21 for rotation.

As shown in FIGS. 3 and 4, included in the impeller position control section 4 are a plurality of electromagnets 41, accommodated in the housing 20, for attracting the second magnetic member 28 of the impeller 21 thereto and a plurality of position sensors 42 for detecting the positions of the second magnetic members 28 of the impeller 21. The electromagnets (three) 41 and the position sensors (three) 42 are spaced at equiangular intervals respectively. The electromagnets 41 and the sensors 42 are also spaced at equiangular intervals. Each of the electromagnets 41 includes a core and a coil. Three electromagnets 41 are arranged in the preferred embodiment, but other quantities, such as, for example, four electromagnets may also be provided. By adjusting the electromagnetic forces of the electromagnets 41 in accordance with results of detection of the position sensors 42, it is possible to balance forces acting on the impeller 21 in a rotational axis (z-axis) direction and control moments about an x-axis and a y-axis both perpendicular to the rotational axis (z-axis).

Each of the position sensors 42 detects the distance of the gap between the electromagnet 41 and the second magnetic member 28. An output of the position sensor 42 indicating the result of the detection is sent to a control part 51 of the control mechanism 6 for controlling electric current to be applied to the coil of the electromagnet (hereinafter referred to as electromagnet current) or a voltage to be applied thereto. When a radial force such as gravity acts on the impeller 21, the impeller 21 is held at the center of the housing 20 by virtue of restoring forces of a magnetic flux between the permanent magnet 25 of the impeller 21 and the permanent magnet 33 of the rotor 31 and restoring forces of a magnetic flux between the electromagnet 41 and the second magnetic member 28.

Figure 6:
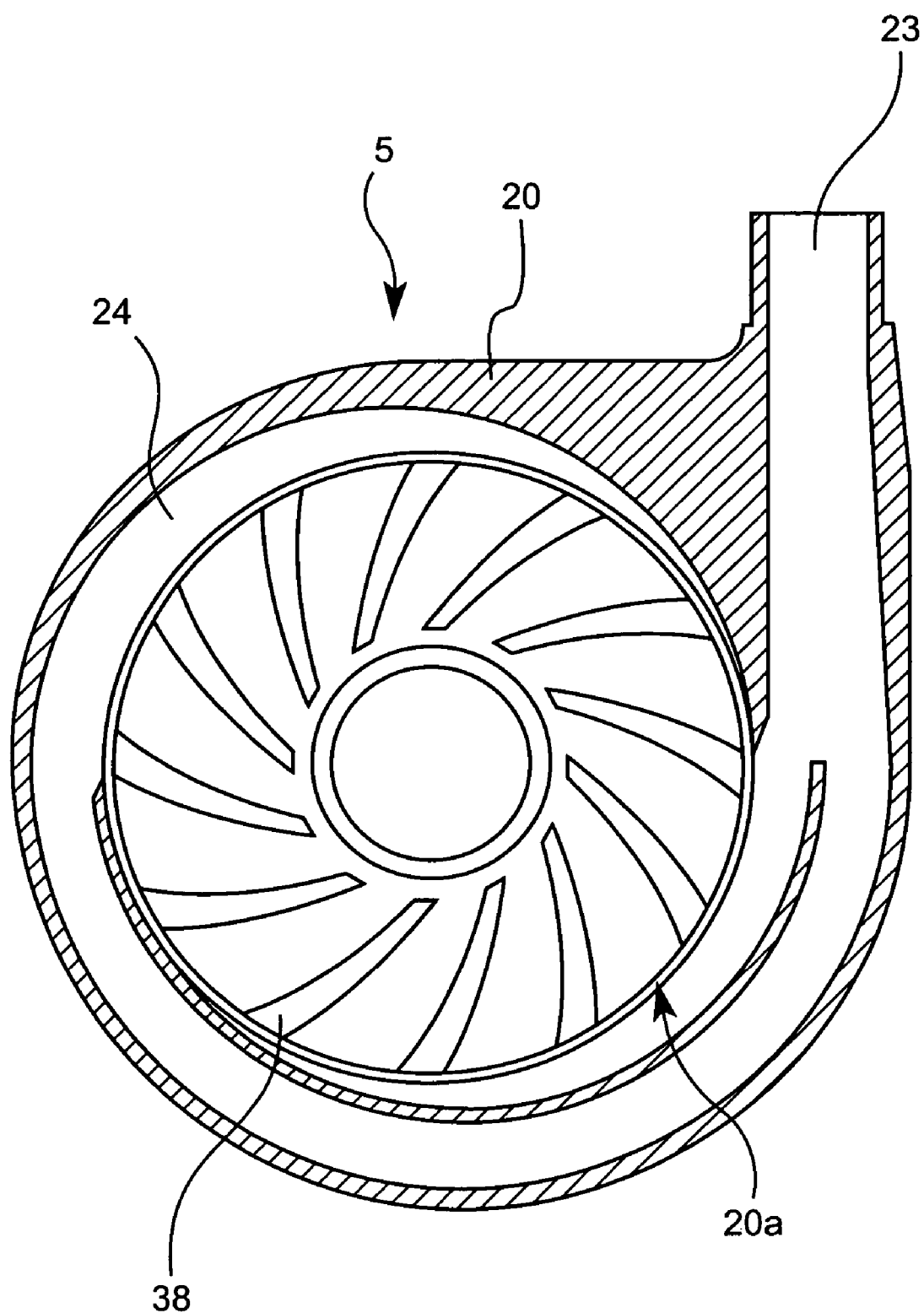
FIG. 6 is a sectional view showing a state in which an impeller has bee removed from the sectional view taken along the line A—A in FIG. 2 showing the body of the centrifugal fluid pump apparatus.

As shown in FIG. 6, in the centrifugal fluid pump apparatus 1 of the embodiment, the housing 20 accommodates the impeller 21 and has the groove 38 for hydrodynamic bearing formed on an inner surface 20a of the housing 20 at the rotor-disposed side, the inner surface 20a of which forms the blood chamber 24. When the operation of the magnetic bearing stops (in other words, when the operation of the electromagnet stops and magnetic levitation state is lost) due to a failure or malfunction, a hydrodynamic levitation effect is generated between the groove 38 for hydrodynamic bearing and the impeller 21, if the rotation of the impeller 21 is maintained at a speed more than a predetermined value, as discussed below, thereby allowing the impeller 21 to rotate without contacting the inner surface of the housing 20.

As shown in FIG. 6, the groove 38 for hydrodynamic bearing has a size corresponding to that of the bottom surface of the impeller 21 (the surface of a rotor side). In the centrifugal fluid pump apparatus 1 of the illustrated embodiment, the groove 38 for hydrodynamic bearing extends spirally (in other words, curved) outwardly to the vicinity of the outer edge of the inner surface 20a, with one end of the groove 38 for hydrodynamic bearing disposed on the circumference of a circle spaced outward at a short distance from the center of the inner surface 20*a* of the housing 20 and with the width thereof becoming outwardly gradually larger. A plurality of the grooves 38 for hydrodynamic bearing has substantially the same configuration and is spaced at almost equal intervals. Each of the grooves 38 for hydrodynamic bearing is concavely formed. It is preferable that the depth thereof is in the range of 0.01 mm to 0.2 mm. It is also preferable that the number of the grooves 38 for hydrodynamic bearing is in the range of six to thirty-six. In the preferred embodiment, twelve grooves 38 for hydrodynamic bearing are provided at equiangular intervals around the center of the axis of the impeller 21.

The groove 38 for hydrodynamic bearing may be disposed on the surface of the impeller 21 at the side of the rotor 31 instead of disposing it on the housing 20. It is preferable that the groove 38 for hydrodynamic bearing disposed on the surface of the impeller 21 at the side of the rotor 31 has the same construction as that of the groove 38 for hydrodynamic bearing disposed on the inner surface of the housing 20.

The groove 38 for hydrodynamic bearing having the above-described construction is attracted toward the impeller torque generation section 3, when the impeller position control section 4 does not operate. Owing to the hydrodynamic bearing effect generated between the groove 38 for hydrodynamic bearing and the bottom surface of the impeller 21 (or between the groove 38 for hydrodynamic bearing and the inner surface of the housing), the impeller 21 rotates at a position spaced at a short distance from the inner surface of the housing 20 without contacting the inner surface thereof, thus providing a blood passage between the lower surface of the impeller 21 and the inner surface of the housing 20. Thereby it is possible to prevent blood from staying therebetween and thrombus from occurring owing to the stay of the blood therebetween. In addition, the groove 38 for hydrodynamic bearing displays an agitating action between the lower surface of the impeller 21 and the inner surface of the housing 20 in a normal state, thus preventing the blood from partially staying therebetween.

With reference to FIG. 1, the control mechanism 6 includes a power amplifier 52 for the magnetic coupling motor 34, a motor control circuit 53, a power amplifier 54 for the electromagnet 41, the electromagnet current monitoring part 57 for monitoring electric current to be applied to the electromagnet 41, a sensor circuit 55 for the sensor 42, the position sensor output monitoring part 56 for monitoring the output of the sensor 42, and the control part 51. The control part 51 has the motor current monitoring function.

In the preferred embodiment, the control mechanism 6 has both the electromagnet current monitoring part 57 and the position sensor output monitoring part 56. But alternatively, the control mechanism 6 may have the electromagnet current monitoring part 57 or the position sensor output monitoring part 56.

The centrifugal fluid pump apparatus 1 has an emergency impeller rotation function that operates when the failure detection function detects that the sensor or the electromagnet has a failure and allows the impeller 21 to rotate without contacting the housing 20 by utilizing the groove 38 for hydrodynamic bearing.

The control part 51 has the failure detection function of determining whether the sensor has a failure by using an output of the electromagnet current monitoring part or an output of the sensor output monitoring part; a rotation termination function of terminating current to the motor and the electromagnet 41 when the failure detection function detects a failure to thereby terminate rotation of the rotor 31 and the impeller 21; impeller magnetic counterforce application function to apply a current to the electromagnet 41 sufficient to overcome the magnetic attraction force of the rotor 31 to the impeller 21 caused by the permanent magnet 33; a hydrodynamic levitation control detection function of detecting rotation of the impeller and the rotor by using a motor current monitored by the motor current monitoring function; a motor speed control function for increasing the motor speed and hence the impeller rotation speed up to a predetermined value (for example, gradually, namely, successively or stepwise) after the hydrodynamic levitation control detection function detects that the hydraulic bearing coupling between the impeller and the rotor has been made; and impeller magnetic counterforce termination function to terminate current to the electromagnet 41 once the predetermined impeller rotation speed is reached.

The control mechanism 6 of the centrifugal pump of the embodiment has the position sensor output monitoring function and the electromagnet current monitoring function. When the control mechanism 6 detects that an output of the position sensor (plural systems are provided) or electromagnet current (plural systems are provided) deviates from a normal range, which means that control of the magnetic bearing cannot be performed owing to the magnetic levitation failure, the control mechanism 6 shifts the non-contact rotation of the impeller by means of the magnetic bearing to the non-contact rotation thereof by means of the groove 38 for hydrodynamic bearing.

If the sensor system of the magnetic bearing has a failure owing to breakage of devices or disconnection of cables, the output of the sensor deviates from its normal range. For example, if a reluctance sensor has disconnection, the output thereof deviates from its normal range.

Thus, the centrifugal fluid pump apparatus of the embodiment has a sensor circuit having a function of generating a predetermined output value exceeding the normal level when the sensor system has disconnection. More specifically, in the case where the normal range of the output of the sensor circuit is in the range of −1 to +1 [V] as the output of the sensor, the output of the sensor circuit is +2.5 [V] (predetermined value) when the sensor system has disconnection. Therefore the failure detection function is capable of determining easily and securely that the sensor has a failure (disconnection), when an output value of the sensor monitored by the sensor output monitoring function is equal to the predetermined output value at the time when the sensor system has disconnection.

Similar to the sensor system, if the electromagnet current system has a failure owing to breakage of devices or disconnection of cables, electric current to be applied to the electromagnet current system deviates from its normal range. Therefore, the centrifugal fluid pump apparatus of the embodiment has a circuit for the electromagnet. The electromagnet circuit used in the preferred embodiment is of a type not energized when the electromagnet has disconnection. More specifically, the normal range of electric current to be applied to the electromagnet circuit is in the range of 1 to 2 [A]. When the electromagnet circuit has disconnection, an electric current of 0 [A] is applied thereto. Accordingly, the failure detection function is capable of determining easily and securely that the electromagnet has a failure (disconnection), when the electromagnet current monitoring function monitors that electric current is not applied to the electromagnet circuit.

The centrifugal fluid pump apparatus of the embodiment has a plurality of electromagnets. The electromagnet monitoring function monitors the output of each of the electromagnets. If any one of the electromagnets has a failure, the failure detection function determines that the electromagnet has a failure. Similarly, the centrifugal fluid pump apparatus of the embodiment has a plurality of position sensors. The sensor output monitoring function monitors the output of each of the position sensors. If any one of the position sensors, the failure detection function determines that the position sensor has a failure.

The dynamic pressure bearing constructed of the groove for hydrodynamic levitation control is a system of maintaining the non-contact between the impeller 21 and the housing 20 by virtue of the pressure generated by the groove for hydrodynamic bearing, which thereby establishes a hydraulic bearing coupling. To generate sufficient pressure and thus establish the hydraulic bearing coupling, the impeller 21 is required to rotate at more than a certain speed. To be able to rotate, however, the magnetic coupling between the impeller and the rotor should be normal. If a failure has occurred in the control system of the magnetic bearing, the magnetic coupling between the impeller and the rotor becomes abnormal. In the centrifugal fluid pump apparatus of the present invention, the impeller is capable of accomplishing a stable non-contact rotation by means of the groove for hydrodynamic bearing, when the impeller speed (the rotor speed) is in the range of 1000 to 3000 rpm, preferably about 1200 rpm.

The emergency impeller rotation function that operates after a failure is detected will be described below.

In the centrifugal fluid pump apparatus of the present invention, when the failure detection function detects a failure, the current to the motor and to the electromagnet 41 is stopped and one waits for termination of rotation of the impeller. Consequently, the impeller 21 is attracted toward the rotor 31 and approaches the inner surface of the housing 20 due to the unbalanced magnetic attraction force from permanent magnet 33. More specifically, the impeller 21 becomes strongly magnetically attracted to the rotor 31 and encounters strong frictional forces such that it is unable to freely rotate.

The impeller magnetic counterforce application function applies a current to the electromagnet 41 sufficient to overcome the magnetic attraction force of the rotor 31 to the impeller 21 caused by the permanent magnet 33, and thereby loosen the impeller 21 from the rotor 31. Once the coupling of the impeller from the magnet is loosened, the impeller will be able to rotate and the hydrodynamic control system will engage. Preferably, the initial current applied to the electromagnet 41 to create the counterforce is applied using pulse width modulation (PWM) control at a 10% duty cycle, i.e., 10% on time.

After applying a 10% duration current to the electromagnetic coil to create a counterforce, a first attempt is made to start rotating the impeller by applying a predetermined start-up voltage to the motor, for example 4.4 volts. If the motor fails to achieve rotation of the impeller after the first attempt, the duration time for the counterforce is increased, preferably by 1% step size to, for example 11% duty cycle, and a second attempt is made to start up rotation of the impeller. This process is repeated until rotation of the impeller is achieved, or an upper limit of duration time percentage, such as 20% on time, is reached.

By using a hydrodynamic levitation control detection function for detecting rotation of the impeller and the rotor and applying a motor current as monitored by the motor current monitoring function, the hydrodynamic levitation control between the impeller 21 and the rotor 31 can been detected. More specifically, when hydrodynamic control between the impeller 21 and the rotor 31 is achieved, i.e., there is a hydraulic bearing coupling, the load to the motor increases. Consequently the motor current rises, which allows the detection of a normal magnetic rotational coupling therebetween under hydraulic bearing conditions.

The centrifugal fluid pump apparatus of the present invention has a motor speed control function for increasing the motor speed and hence the impeller rotation speed up to a predetermined value (for example, gradually, namely, successively or stepwise). This function operates after the hydrodynamic levitation control detection function detects that the hydraulic bearing coupling between the impeller and the rotor has been made. This function increases the motor speed up to a predetermined one (at least the motor speed at which substantial non-contact rotation of the impeller by means of the groove for hydrodynamic bearing is allowed). It is preferable that the centrifugal fluid pump apparatus (in other words, the control mechanism) has a motor speed storing function at the time when the failure detection function detects a failure or at a time in the neighborhood of the time when the failure detection function detects the failure. It is also preferable that the motor speed control function increases the motor speed to the one stored by the motor speed storing function or to a predetermined set speed.

The impeller magnetic counterforce termination function terminates current to the electromagnet 41 once the predetermined impeller rotation speed is reached. Thus, when the failure detection function detects that the sensor 42 or the electromagnet 41 has a failure, the emergency impeller rotation function of the centrifugal fluid pump apparatus allows the rotor 31 to rotate, with the impeller 21 in contact with the surface of the housing 20 opposite to the rotor-disposed side by attracting the impeller 21 to the electromagnet 41 with a counterforce. This function releases the state in which the impeller 21 is in contact with the inner surface of the housing at the rotor side and allows the shift preferably to the rotation of the impeller 21 that is made by utilizing the hydrodynamic bearing. After establishing hydrodynamic control of the impeller, there is no longer a need for the continued magnetic counterforce, and current to the electromagnet 41 is terminated.

Figure 7A:
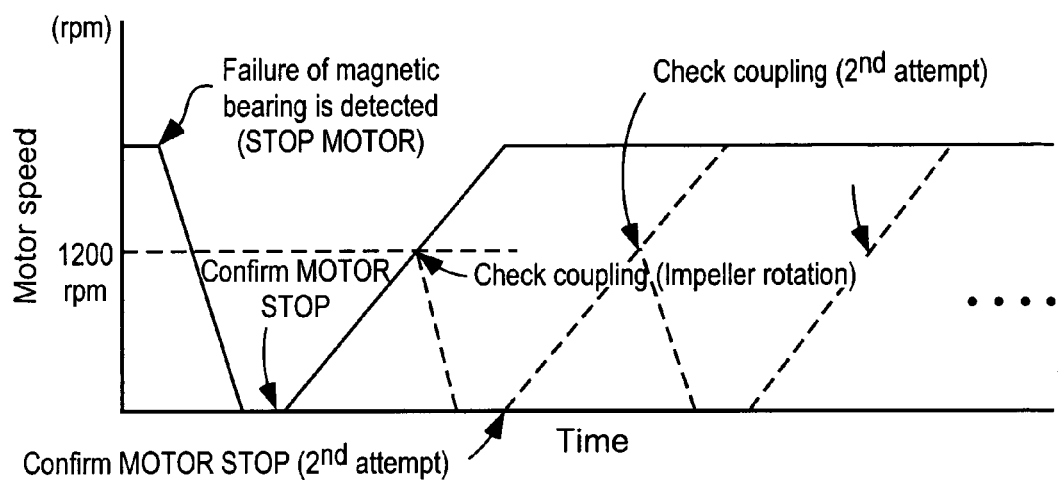
FIGS. 7A and 7B are timing charts for describing the operation of the centrifugal fluid pump apparatus of an embodiment of the present invention.
Figure 7B:
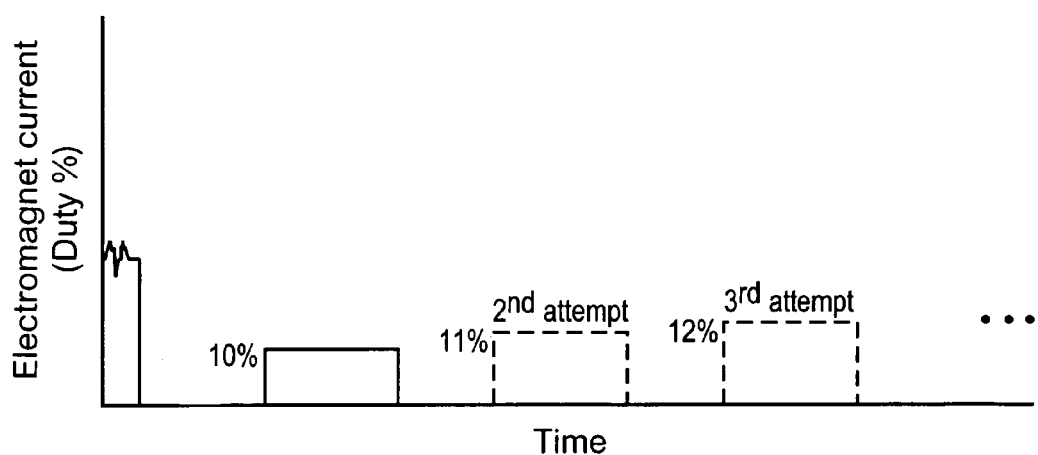

The emergency impeller rotation control mode shown in FIG. 8 and the timing thereof as shown in FIGS. 7A and 7B is described below.

Figure 8:
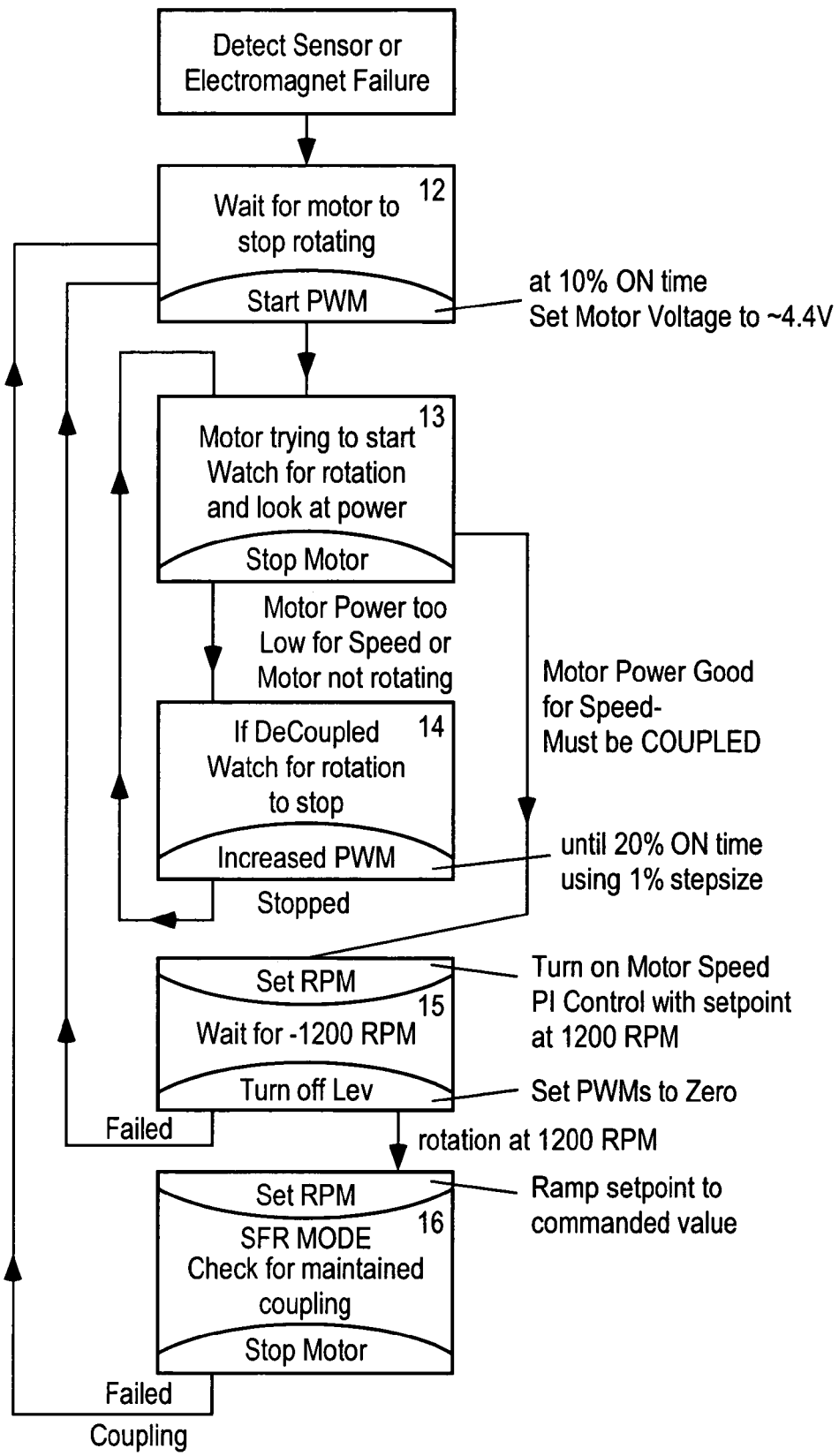
FIG. 8 is a flowchart for describing the operation of the centrifugal fluid pump apparatus of the present invention.

When the failure detection function of the control part 51 detects that the sensor 42 or the electromagnet 41 has a failure (step 11), the emergency rotation control mode is triggered, as shown in FIG. 8, and the operation of the electromagnet and the motor is stopped (step 12). Thereafter, the electromagnet duration time is initiated at a predetermined level to bring the impeller 21 out of contact with the rotor 31. If any one or two, or more depending upon the specific construction, of the electromagnets fails, such a state can be generated by using the remaining electromagnet(s).

Thereafter, in this state, the motor is rotated at a predetermined motor voltage. In other words, at steps 13 and 14, the motor is rotated in order to bring the impeller out of contact with the rotor. If the motor power is too low or if the motor is not rotating the impeller, due to the increased friction for instance, the electromagnetic duration time is incrementally increased, e.g., in 1% increments, in order to increase the magnetic counterforce and thereby reduce the frictional forces on the impeller.

If the hydrodynamic levitation control detection function of the control part 51 determines that the impeller levitation coupling has been achieved, as shown at step 15 in FIG. 8, the impeller magnetic counterforce termination function terminates current to the electromagnet 41 once the predetermined impeller rotation speed is reached, i.e., 1200 rpm. Thereafter, the desired rotation of the impeller is maintained in single fault recovery (SFR) mode, as shown at step 16, which continues to monitor for a failed levitational coupling.

The centrifugal fluid pump apparatus of this invention includes the position sensor output monitoring function or the electromagnet current monitoring function; the motor current monitoring function; the failure detection function for determining a failure of the sensor by using said position sensor output monitoring function or a failure of the electromagnet by using said electromagnet current monitoring function; and the emergency impeller rotation function operating when the failure detection function detects that the sensor has a failure to rotate the impeller by utilizing the groove for hydrodynamic bearing without substantial contact between the impeller and the housing. The emergency impeller rotation function has the rotation termination function of terminating power to the motor and the electromagnet 41 when the failure detection function detects a failure to thereby terminate rotation of the rotor 31 and the impeller 21; impeller magnetic counterforce application function to apply a current to the electromagnet 41 sufficient to overcome the magnetic attraction force of the rotor 31 to the impeller 21 caused by the permanent magnet 33; hydrodynamic levitation control detection function of detecting rotation of the impeller and the rotor by using a motor current monitored by the motor current monitoring function; motor speed control function for increasing the motor speed and hence the impeller rotation speed up to a predetermined value (for example, gradually, namely, successively or stepwise) after the hydrodynamic levitation control detection function detects that the hydraulic bearing coupling between the impeller and the rotor has been made; and impeller magnetic counterforce termination function to terminate current to the electromagnet 41 once the predetermined impeller rotation speed is reached.

Thereby in the case where the position sensor or the electromagnet which constitute the control system of the magnetic bearing have trouble and experience a failure or other malfunction, it is possible to shift the rotation of the impeller that is made by the magnetic bearing to the rotation thereof that is made by utilizing the pressure generated by the groove for hydrodynamic bearing. Thus, it is possible to maintain feeding of a liquid.

Figure 9:
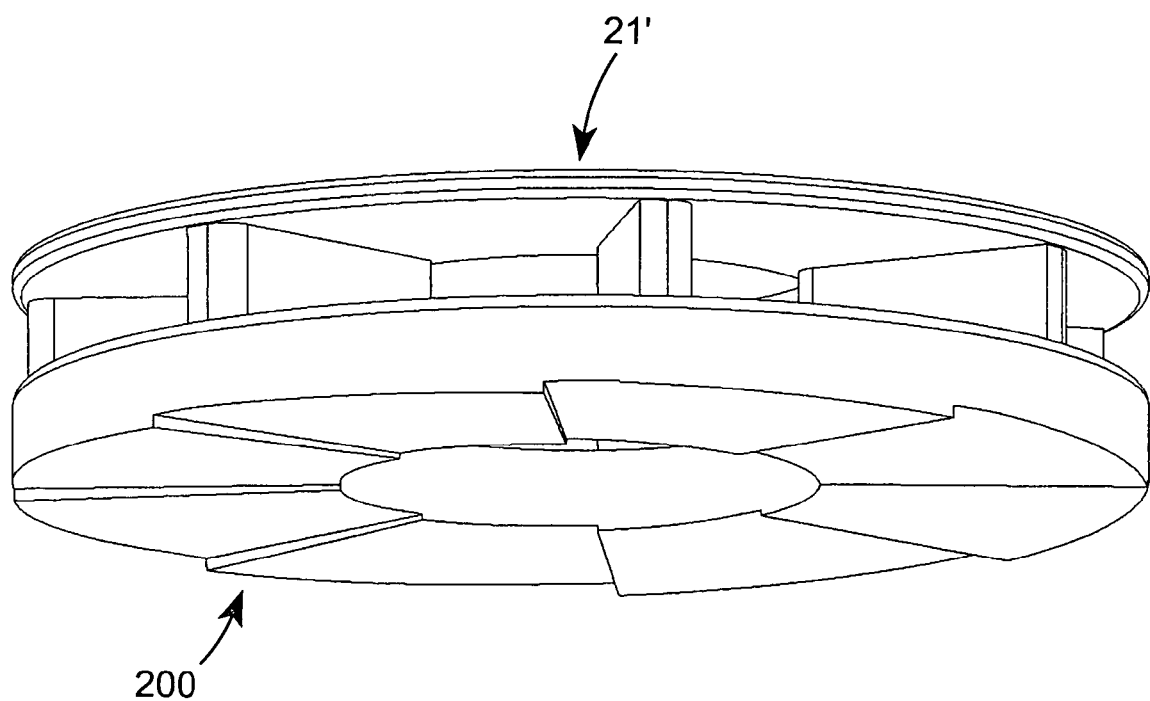
FIG. 9 is a perspective view of an alternative embodiment of an impeller for the centrifugal fluid pump apparatus of the present invention.

An alternative embodiment, as shown in FIG. 9, utilizes an impeller 21' which similarly rotates without contacting the housing 20. Impeller 21' is substantially the same as impeller 21, except that there is no groove 38 for hydrodynamic bearing provided on a surface of the impeller 21' at the side of the rotor 31. Instead, impeller 21' includes a plurality of steps 200 for hydrodynamic bearing at the side of the rotor 31, and the inner surface of the housing 20 at the side of the rotor 31 is substantially smooth. As described above for the first embodiment of impeller 21, owing to the hydrodynamic bearing effect generated between the steps 200 and the inner surface of the housing, the impeller 21' rotates at a position spaced at a short distance from the inner surface of the housing 20 without contacting the inner surface thereof, thus providing a blood passage between the lower surface of the impeller 21' and the inner surface of the housing 20. The functioning and operation of a centrifugal fluid pump apparatus having the impeller 21' is identical to that described above, except that the steps 200 define the hydrodynamic bearing rather than the grooves 38.

While the preferred form of the present invention has been described, it is to be understood that modifications will be apparent to those skilled in the art without departing from the spirit of the invention. The scope of the invention, therefore, is to be determined solely by the following claims.

What is claimed is:

1. A centrifugal fluid pump apparatus comprising a pump body in which an impeller rotates without contacting a housing; and a control mechanism for said pump body,
   said pump body including:
   said housing having a blood inlet port and a blood outlet port;
   a centrifugal pump section including an impeller having a first magnetic material and a second magnetic material and rotating in said housing to feed a fluid by a centrifugal force generated during its rotation;
   an impeller rotational torque generation section including a rotor having a magnet for attracting said first magnetic material of said impeller and a motor for rotating said rotor;
   an impeller position control section having an electromagnet for attracting said second magnetic material of said impeller;
   a position sensor for detecting a position of said impeller; and
   hydrodynamic bearing means provided on an inner surface of said housing at a side of said rotor or on a surface of said impeller at a side of said rotor,
   said control mechanism comprising:
   a position sensor output monitoring function or an electromagnet current monitoring function;
   a motor current monitoring function;
   a failure detection function for determining a failure of the sensor by using said position sensor output monitoring function or a failure of the electromagnet by using said electromagnet current monitoring function; and
   an emergency impeller rotation function operating when said failure detection function detects the failure of the sensor or the failure of the electromagnet to rotate said impeller by utilizing said hydrodynamic bearing means without substantial contact between said impeller and said housing,
   wherein said emergency impeller rotation function has:
   rotation termination function of terminating power to the motor and the electromagnet when the failure detection function detects a failure to thereby terminate rotation of the rotor and the impeller;
   impeller magnetic counterforce application function to apply a current to the electromagnet sufficient to overcome the magnetic coupling force of the rotor to the impeller caused by the magnet;
   hydrodynamic levitation control detection function of detecting hydraulic bearing coupling and thereby magnetic rotational coupling of the impeller and the rotor under hydraulic bearing conditions by using a motor current monitored by the motor current monitoring function;
   motor speed control function for increasing the motor speed and hence the impeller rotation speed up to a predetermined value after the hydraulic levitation control detection function detects that the hydraulic bearing coupling between the impeller and the rotor has been made; and
   impeller magnetic counterforce termination function to terminate current to the electromagnet once the predetermined impeller rotation speed is reached.

2. A centrifugal fluid pump apparatus according to claim 1, wherein said control mechanism has said position sensor output monitoring function and said electromagnet current monitoring function and said failure detection function can determine the failure of the sensor and the failure of the electromagnet.

3. A centrifugal fluid pump apparatus according to claim 1, further comprising a sensor circuit for said sensor, wherein said sensor circuit has a function of generating an output having a predetermined value exceeding a normal level when said sensor has disconnection, and said failure detection function determines whether said sensor has a failure, based on an output of said sensor monitored by said sensor output monitoring function.

4. A centrifugal fluid pump apparatus according to claim 1, further comprising an electromagnet circuit for said electromagnet, wherein said electromagnet circuit is not energized when said electromagnet has disconnection, and said failure detection function determines that said electromagnet has a failure when said electromagnet current monitoring function monitors that electric current is not applied to said electromagnet circuit.

5. A centrifugal fluid pump apparatus according to claim 1, wherein when said failure detection function detects a failure, said emergency impeller rotation function allows said impeller to rotate by balancing the magnetic coupling force between the magnet of said rotor and said impeller and the counterforce generated by said electromagnet.

6. A centrifugal fluid pump apparatus according to claim 1, wherein said hydrodynamic bearing means includes at least one groove provided on the inner surface of said housing at a side of said rotor.

7. A centrifugal fluid pump apparatus according to claim 1, wherein said hydrodynamic bearing means includes at least one groove provided on the surface of said impeller at a side of said rotor.

8. A centrifugal fluid pump apparatus according to claim 1, wherein said hydrodynamic bearing means includes a plurality of steps provided on the surface of said impeller at a side of said rotor.

9. A centrifugal fluid pump apparatus according to claim 1, wherein said impeller magnetic counterforce application function comprises applying a first duration current to the electromagnet to create a counterforce and attempting to rotate the impeller by applying a predetermined voltage to the motor.

10. A centrifugal fluid pump apparatus according to claim 9, wherein when the motor fails to achieve rotation of the impeller after the first attempt, said impeller magnetic counterforce application function further comprises applying a second duration current to the electromagnet to create the counterforce and attempting to rotate the impeller by applying the predetermined voltage to the motor, wherein said second duration current is greater than said first duration current such that the counterforce created with said second duration current is greater than the counterforce created with said first duration current.

11. A centrifugal fluid pump apparatus according to claim 10, wherein said second duration current is greater than said first duration current by a predetermined step value.

12. A centrifugal fluid pump apparatus according to claim 11, wherein when the motor fails to achieve rotation of the impeller after the first and second attempts, said impeller magnetic counterforce application function further comprises repeatedly applying an increased duration current to the electromagnet to create the counterforce and attempting to rotate the impeller by applying the predetermined voltage to the motor, said increased duration current being repeatedly increased by the predetermined step value until one of rotation of the impeller is achieved or said increased duration current reaches a predetermined maximum value.

13. A centrifugal fluid pump apparatus according to claim 12, wherein said first duration current is a 10% on time duty cycle.

14. A centrifugal fluid pump apparatus according to claim 12, wherein the predetermined step value is 1%.

15. A centrifugal fluid pump apparatus according to claim 12, wherein the predetermined maximum value of said increased duration current is approximately 20% on time.

* * * * *